United States Patent
Mika et al.

(10) Patent No.: US 10,342,982 B2
(45) Date of Patent: Jul. 9, 2019

(54) METHODS AND SYSTEMS FOR TREATING CARDIAC MALFUNCTION

(71) Applicant: BackBeat Medical, Inc., New Hope, PA (US)

(72) Inventors: Yuval Mika, Closter, NJ (US); Darren Sherman, Fort Lauderdale, FL (US); Daniel Burkhoff, Manhattan, NY (US)

(73) Assignee: BackBeat Medical, Inc., New Hope, PA (US)

( * ) Notice: Subject to any disclaimer, the term of this patent is extended or adjusted under 35 U.S.C. 154(b) by 0 days.

(21) Appl. No.: 15/259,282

(22) Filed: Sep. 8, 2016

(65) Prior Publication Data

US 2017/0072203 A1    Mar. 16, 2017

Related U.S. Application Data (60) Provisional application No. 62/217,299, filed on Sep. 11, 2015.

(51) Int. Cl.
| | | |
|---|---|---|
| *A61N 1/365* | (2006.01) | |
| *A61N 1/362* | (2006.01) | |
| *A61N 1/368* | (2006.01) | |

(52) U.S. Cl.
CPC ....... *A61N 1/36564* (2013.01); *A61N 1/3627* (2013.01); *A61N 1/368* (2013.01); *A61N 1/36571* (2013.01); *A61N 1/36585* (2013.01)

(58) Field of Classification Search
CPC . A61N 1/36564; A61N 1/365; A61N 1/36571
See application file for complete search history.

(56) References Cited

U.S. PATENT DOCUMENTS

| | | |
|---|---|---|
| 3,683,934 A | 8/1972 | Bohdan et al. |
| 3,814,106 A | 6/1974 | Berkovits |

(Continued)

FOREIGN PATENT DOCUMENTS

| | | |
|---|---|---|
| AU | 2013361318 | 8/2018 |
| CA | 2933278 A1 | 6/2015 |

(Continued)

OTHER PUBLICATIONS

Notice of Allowance dated Mar. 15, 2017 in U.S. Appl. No. 15/163,078.

(Continued)

*Primary Examiner* — William J Levicky
(74) *Attorney, Agent, or Firm* — Plumsea Law Group, LLC (57) ABSTRACT

Methods and systems for treating cardiac malfunction are disclosed, which according to an embodiment, may involve delivering a stimulation pattern of stimulation pulses to at least one cardiac chamber of a heart, with at least one of the stimulation pulses having a first stimulation setting configured to reduce at least one of end systolic volume (ESV) and end diastolic volume (EDV) in the heart and at least one of the stimulation pulses having a second stimulation setting different from the first stimulation setting, and with the stimulation pattern being configured to reduce the at least one of end systolic volume (ESV) and end diastolic volume (EDV) by at least 5% and maintain the at least one of end systolic volume (ESV) and end diastolic volume (EDV) on average at such reduced volume for a time period of at least one hour.

30 Claims, 8 Drawing Sheets

(56) References Cited

U.S. PATENT DOCUMENTS

| | | | |
|---|---|---|---|
| 3,939,844 A | 2/1976 | Pequignot | |
| 4,407,287 A | 10/1983 | Herpers | |
| 4,712,555 A | 12/1987 | Thornander et al. | |
| 4,719,921 A | 1/1988 | Chirife | |
| 4,899,752 A | 2/1990 | Cohen | |
| 5,063,239 A | 11/1991 | Schwenner et al. | |
| 5,163,429 A | 11/1992 | Cohen | |
| 5,213,098 A | 5/1993 | Bennett et al. | |
| 5,318,595 A | 6/1994 | Ferek-Petric et al. | |
| 5,584,868 A | 12/1996 | Salo et al. | |
| 5,601,613 A | 2/1997 | Florio et al. | |
| 5,601,615 A | 2/1997 | Markowitz et al. | |
| 5,612,380 A | 3/1997 | Lerner et al. | |
| 5,713,928 A | 2/1998 | Bonnet et al. | |
| 5,800,334 A | 9/1998 | Wilk | |
| 5,891,176 A | 4/1999 | Bornzin | |
| 5,928,271 A | 7/1999 | Hess et al. | |
| 5,971,911 A | 10/1999 | Wilk | |
| 6,045,531 A | 4/2000 | Davis | |
| 6,241,678 B1 | 6/2001 | Afremov et al. | |
| 6,271,015 B1 | 8/2001 | Gilula et al. | |
| 6,314,322 B1 | 11/2001 | Rosenberg | |
| 6,377,852 B1 | 4/2002 | Bornzin et al. | |
| 6,450,942 B1 | 9/2002 | Lapanashvili et al. | |
| 6,507,756 B1 | 1/2003 | Heynen et al. | |
| 6,580,946 B2 | 6/2003 | Struble | |
| 6,628,988 B2 | 9/2003 | Kramer et al. | |
| 6,666,826 B2 | 12/2003 | Salo et al. | |
| 6,668,195 B2 | 12/2003 | Warman et al. | |
| 6,699,682 B2 | 3/2004 | Gilula et al. | |
| 6,701,187 B1 | 3/2004 | Bornzin et al. | |
| 6,795,732 B2 | 9/2004 | Stadler et al. | |
| 6,832,113 B2 | 12/2004 | Belalcazar | |
| 7,001,611 B2 | 2/2006 | Kiso et al. | |
| 7,092,759 B2 | 8/2006 | Nehls et al. | |
| 7,096,064 B2 | 8/2006 | Deno et al. | |
| 7,098,233 B2 | 8/2006 | Maria et al. | |
| 7,103,410 B2 | 9/2006 | Kramer et al. | |
| 7,184,832 B2 | 2/2007 | Deno et al. | |
| 7,233,824 B2 | 6/2007 | Kleckner et al. | |
| 7,286,873 B2 | 10/2007 | Havel et al. | |
| 7,289,849 B2 | 10/2007 | Baynham et al. | |
| 7,346,394 B2 | 3/2008 | Liu et al. | |
| 7,348,173 B2 | 3/2008 | Gilula et al. | |
| 7,363,077 B1 * | 4/2008 | Min | A61N 1/3627 607/23 |
| 7,548,782 B2 | 6/2009 | Kramer et al. | |
| 7,618,364 B2 | 11/2009 | Walsh et al. | |
| 7,651,461 B2 | 1/2010 | Alferness et al. | |
| 7,674,222 B2 | 3/2010 | Nikolic et al. | |
| 7,676,264 B1 | 3/2010 | Pillai et al. | |
| 7,711,420 B2 | 5/2010 | Baynham et al. | |
| 7,725,173 B2 | 5/2010 | Viertio-Oja et al. | |
| 7,725,185 B2 | 5/2010 | Liu et al. | |
| 7,765,008 B2 | 7/2010 | Ben-Haim et al. | |
| 7,869,874 B2 | 1/2011 | Levin et al. | |
| 8,027,724 B2 | 9/2011 | Wei et al. | |
| 8,046,070 B2 | 10/2011 | Salo et al. | |
| 8,086,315 B2 | 12/2011 | Schwartz et al. | |
| 8,165,674 B2 | 4/2012 | Levin et al. | |
| 8,187,160 B2 | 5/2012 | Criscione et al. | |
| 8,340,763 B2 | 12/2012 | Levin et al. | |
| 8,428,729 B2 | 4/2013 | Schwartz et al. | |
| 8,515,536 B2 | 8/2013 | Levin et al. | |
| 8,521,280 B2 | 8/2013 | Levin et al. | |
| 9,008,769 B2 | 4/2015 | Mika et al. | |
| 9,320,903 B2 | 4/2016 | Schwartz et al. | |
| 9,333,352 B2 | 5/2016 | Mika et al. | |
| 9,370,661 B2 | 6/2016 | Levin et al. | |
| 9,370,662 B2 | 6/2016 | Mika et al. | |
| 9,427,586 B2 | 8/2016 | Levin et al. | |
| 9,526,900 B2 | 12/2016 | Mika et al. | |
| 9,656,086 B2 | 5/2017 | Mika et al. | |
| 9,687,636 B2 | 6/2017 | Levin et al. | |
| 9,731,136 B2 | 8/2017 | Levin et al. | |
| 9,878,162 B2 | 1/2018 | Mika et al. | |
| 9,937,351 B2 | 4/2018 | Mika et al. | |
| 10,071,250 B2 | 9/2018 | Mika et al. | |
| 10,232,183 B2 | 3/2019 | Schwartz et al. | |
| 10,252,060 B2 | 4/2019 | Levin et al. | |
| 10,252,061 B2 | 4/2019 | Mika et al. | |
| 2002/0161410 A1 | 10/2002 | Kramer et al. | |
| 2002/0173826 A1 | 11/2002 | Lincoln et al. | |
| 2003/0060858 A1 | 3/2003 | Kieval et al. | |
| 2003/0083700 A1 | 5/2003 | Hill et al. | |
| 2003/0144702 A1 | 7/2003 | Yu et al. | |
| 2003/0144703 A1 | 7/2003 | Yu et al. | |
| 2003/0176896 A1 | 9/2003 | Lincoln et al. | |
| 2003/0199934 A1 | 10/2003 | Struble et al. | |
| 2004/0015081 A1 | 1/2004 | Kramer et al. | |
| 2004/0044361 A1 | 3/2004 | Frazier et al. | |
| 2004/0049235 A1 | 3/2004 | Deno et al. | |
| 2004/0138715 A1 | 7/2004 | Van Groeningen et al. | |
| 2004/0167410 A1 | 8/2004 | Hettrick | |
| 2004/0186523 A1 | 9/2004 | Florio | |
| 2004/0215255 A1 | 10/2004 | Vries | |
| 2004/0215266 A1 | 10/2004 | Struble et al. | |
| 2004/0215268 A1 | 10/2004 | Corbucci | |
| 2005/0038478 A1 | 2/2005 | Klepfer et al. | |
| 2005/0070952 A1 | 3/2005 | Devellian | |
| 2005/0075676 A1 | 4/2005 | Deno et al. | |
| 2005/0090872 A1 | 4/2005 | Deno et al. | |
| 2005/0101998 A1 | 5/2005 | Kleckner et al. | |
| 2005/0102002 A1 | 5/2005 | Salo et al. | |
| 2005/0119285 A1 | 6/2005 | Matos et al. | |
| 2005/0143785 A1 | 6/2005 | Libbus | |
| 2005/0149130 A1 | 7/2005 | Libbus | |
| 2005/0149131 A1 | 7/2005 | Libbus et al. | |
| 2005/0222640 A1 | 10/2005 | Schwartz et al. | |
| 2005/0234543 A1 | 10/2005 | Glaser et al. | |
| 2006/0173502 A1 | 8/2006 | Baynham et al. | |
| 2006/0173504 A1 | 8/2006 | Zhu et al. | |
| 2006/0247702 A1 | 11/2006 | Stegemann et al. | |
| 2006/0264980 A1 | 11/2006 | Khairkhahan et al. | |
| 2007/0073352 A1 | 3/2007 | Euler et al. | |
| 2007/0083243 A1 | 4/2007 | Prakash et al. | |
| 2007/0299475 A1 | 12/2007 | Levin et al. | |
| 2007/0299477 A1 | 12/2007 | Kleckner et al. | |
| 2008/0027488 A1 | 1/2008 | Coles et al. | |
| 2008/0077187 A1 | 3/2008 | Levin et al. | |
| 2008/0109043 A1 | 5/2008 | Salo et al. | |
| 2009/0018608 A1 | 1/2009 | Schwartz et al. | |
| 2009/0036940 A1 | 2/2009 | Wei et al. | |
| 2009/0069859 A1 | 3/2009 | Whinnett et al. | |
| 2009/0082823 A1 | 3/2009 | Shuros et al. | |
| 2009/0118783 A1 | 5/2009 | Patangay et al. | |
| 2009/0207028 A1 | 8/2009 | Kubey et al. | |
| 2009/0240298 A1 | 9/2009 | Lian et al. | |
| 2009/0247893 A1 | 10/2009 | Lapinlampi et al. | |
| 2009/0254141 A1 | 10/2009 | Kramer et al. | |
| 2009/0281440 A1 | 11/2009 | Farazi et al. | |
| 2009/0281591 A1 | 11/2009 | Shuros et al. | |
| 2009/0318995 A1 | 12/2009 | Keel et al. | |
| 2010/0069989 A1 | 3/2010 | Shipley et al. | |
| 2010/0087889 A1 | 4/2010 | Maskara et al. | |
| 2010/0094370 A1 | 4/2010 | Levin et al. | |
| 2010/0121397 A1 | 5/2010 | Cholette | |
| 2010/0121402 A1 | 5/2010 | Arcot-Krishnamurthy et al. | |
| 2010/0204741 A1 | 8/2010 | Tweden et al. | |
| 2011/0144712 A1 | 6/2011 | Stahmann et al. | |
| 2011/0160787 A1 | 6/2011 | Greenhut et al. | |
| 2011/0172731 A1 | 7/2011 | Levin et al. | |
| 2012/0041502 A1 | 2/2012 | Schwartz et al. | |
| 2012/0109237 A1 | 5/2012 | Xiao et al. | |
| 2012/0215272 A1 | 8/2012 | Levin et al. | |
| 2013/0304149 A1 | 11/2013 | Kass et al. | |
| 2013/0331901 A1 | 12/2013 | Levin et al. | |
| 2014/0128934 A1 | 5/2014 | Schwartz et al. | |
| 2014/0163600 A1 | 6/2014 | Levin et al. | |
| 2014/0163636 A1 | 6/2014 | Levin et al. | |
| 2014/0180353 A1 * | 6/2014 | Mika | A61N 1/36564 607/17 |
| 2016/0129084 A1 * | 5/2016 | Caggiano | A61K 38/1883 514/9.6 |

(56) References Cited

U.S. PATENT DOCUMENTS

| | | | |
|---|---|---|---|
| 2016/0220824 | A1 | 8/2016 | Schwartz et al. |
| 2016/0243368 | A1 | 8/2016 | Mika et al. |
| 2016/0263383 | A1 | 9/2016 | Levin et al. |
| 2016/0339244 | A1 | 11/2016 | Levin et al. |
| 2017/0080235 | A1 | 3/2017 | Mika et al. |
| 2017/0239481 | A1 | 8/2017 | Mika et al. |
| 2017/0274190 | A1 | 9/2017 | Levin et al. |
| 2017/0291032 | A1 | 10/2017 | Levin et al. |
| 2017/0304048 | A1 | 10/2017 | Mika et al. |
| 2018/0185652 | A1 | 7/2018 | Mika et al. |
| 2018/0256899 | A1 | 9/2018 | Mika et al. |
| 2019/0001141 | A1 | 1/2019 | Mika et al. |

FOREIGN PATENT DOCUMENTS

| | | |
|---|---|---|
| CN | 1662278 A | 8/2005 |
| CN | 101980657 A | 2/2011 |
| CN | 106029165 | 10/2016 |
| CN | 104968392 B | 11/2017 |
| CN | 107715299 A | 2/2018 |
| CN | 108025173 A | 5/2018 |
| CN | 106029165 B | 11/2018 |
| CN | 109364374 A | 2/2019 |
| EP | 0532148 | 3/1993 |
| EP | 2241348 | 10/2010 |
| EP | 2934669 B1 | 6/2017 |
| EP | 3238777 A2 | 11/2017 |
| EP | 3082949 B1 | 11/2018 |
| EP | 3461531 A1 | 4/2019 |
| JP | 2007-519441 A | 7/2007 |
| JP | 2007-531609 A | 11/2007 |
| JP | 2010-508979 A | 3/2010 |
| JP | 2010-512958 A | 4/2010 |
| JP | 2010-536481 A | 12/2010 |
| JP | 2016-540589 A | 12/2016 |
| JP | 2019-042579 | 3/2019 |
| WO | 9944682 A1 | 9/1999 |
| WO | 03000252 A1 | 1/2003 |
| WO | 2009035515 A1 | 3/2005 |
| WO | 2005063332 A1 | 7/2005 |
| WO | 2005097256 A2 | 10/2005 |
| WO | 2007021258 A1 | 2/2007 |
| WO | 2008057631 A1 | 5/2008 |
| WO | 2008079370 A1 | 7/2008 |
| WO | 2012064743 A3 | 5/2012 |
| WO | 2014100429 A2 | 6/2014 |
| WO | 2015094401 A1 | 6/2015 |
| WO | 2017044794 A1 | 3/2017 |
| WO | 2017184912 A2 | 10/2017 |

OTHER PUBLICATIONS

Office Action dated Mar. 24, 2017 in U.S. Appl. No. 15/372,603.
Decision to Grant dated May 26, 2017 in European Patent Application No. 13826807.3.
Arbel E.R., et al., "Successful Treatment of Drug-Resistant Atrial Tachycardia and Intractable Congestive Heart Failure with Permanent Coupled Atrial Pacing," The American Journal of Cardiology, 1978, vol. 41 (2), pp. 336-340.
Auricchio A., et al., "Cardiac Resyncbronization Therapy Restores Optimal Atrioventricular Mechanical Timing in Heart Failure Patients With Ventricular Conduction Delay," Journal of the American College of Cardiology, 2002, vol. 39 (7), pp. 1163-1169.
Auricchio A., et al., "Effect of Pacing Chamber and Atrioventricular Delay on Acute Systolic Function of Paced Patients With Congestive Heart Failure," Circulation—Journal of the American Heart Association, 1999, vol. 99 (23), pp. 2993-3001.
Braunwald E., et al., "Editorial: Paired Electrical Stimulation of the Heart: A Physiologic Riddle and a Clinical Challenge," Circulation, 1965, vol. 32 (5), pp. 677-681.
Calderone A., et al., "The Therapeutic Effect of Natriuretic Peptides in Heart Failure; Differential Regulation of Endothelial and Inducible Nitric Oxide Synthases," Heart Failure Reviews, 2003, vol. 8 (1), pp. 55-70.
Han B., et al., "Cardiovascular Effects of Natriuretic Peptides and Their Interrelation with Endothelin-1," Cardiovascular Drugs and Therapy, 2003, vol. 17 (1), pp. 41-52.
Information Manual, Model 5837 R-Wave Coupled Pulse Generator, Prelim. Ed. III , Medtronic, 1965, 20 pages.
PCT Notification Concerning Transmittal of International Preliminary Report on Patentability (IPER), International Application No. PCT/US2005/028415, from the International Bureau dated Feb. 21, 2008.
International Search Report and Written Opinion for Application No. PCT/US2005/28415, dated Jan. 19, 2006.
International Search Report and Written Opinion for Application No. PCT/US2014/042777, dated Jan. 2, 2015.
Invitation to Pay Additional Fees mailed Oct. 17, 2014 in International Application No. PCT/US2014/042777.
Kerwin W.F., et al., "Ventricular Contraction Abnormalities in Dilated Cardiomyopathy: Effect of Biventricular Pacing to Correct Interventricular Dyssynchrony," Journal of the American College of Cardiology, 2000, vol. 35 (5), pp. 1221-1227.
Lister J.W., et al., "The Hemodynamic Effect of Slowing the Heart Rate by Paired or Coupled Stimulation of the Atria," American Heart Journal, 1967, vol. 73 (3), pp. 362-368.
Liu L. et al., "Left Ventricular Resynchronization Therapy in a Canine Model of Left Bundle Branch Block," American Journal of Physiology—Heart and Circulatory Physiology, 2002, vol. 282 (6), pp. H2238-H2244.
Lopez J.F., et al., "Reducing Heart Rate of the Dog by Electrical Stimulation," Circulation Research, 1964, vol. 15, pp. 414-429.
Nishimura K., et al., "Atrial Pacing Stimulates Secretion of Atrial Natriuretic Polypeptide without Elevation of Atrial Pressure in Awake Dogs with Experimental Complete Atrioventricular Block," Circulation Research, 1990, vol. 66 (1), pp. 115-122.
Notice of Allowance dated Dec. 16, 2014 in U.S. Appl. No. 13/826,215.
O'Cochlain B., et al., "The Effect of Variation in the Interval Between Right and Left Ventricular Activation on Paced QRS Duration," Journal of Pacing and Clinical Electrophysiology, 2001, vol. 24 (12), pp. 1780-1782.
Pappone C., et al., "Cardiac Pacing in Heart Failure Patients with Left Bundle Branch Block: Impact of Pacing Site for Optimizing Left Ventricular Resynchronization," Italian Heart Journal, 2000, vol. 1 (7), pp. 464-469.
PCT Notification of Transmittal of the International Search Report and the Written Opinion of the International Searching Authority; Declaration of Non-Establishment of International Search Report; and PCT Written Opinion of International Searching Authority, dated Apr. 24, 2014 in International Application No. PCT/US2013/076600.
Perego G.B., et al., "Simultaneous Vs. Sequential Biventricular Pacing in Dilated Cardiomyopathy: An Acute Hemodynamic Study," The European Journal of Heart Failure, 2003, vol. 5 (3), pp. 305-313.
Schoonderwoerd B.A., et al., "Atrial Natriuretic Peptides During Experimental Atrial Tachycardia: Role of Developing Tachycardiomyopathy," Journal of Cardiovascular Electrophysiology, 2004, vol. 15 (8), pp. 927-932.
Siddons et al., Cardiac Pacemakers, Pub. No. 680 of American Lecture Series, 1968, Thomas C. Publisher, pp. 200-217.
Verbeek X.A., et al., "Intra-Ventricular Resynchronization for Optimal Left Ventricular Function During Pacing in Experimental Left Bundle Branch Block," Journal of American College of Cardiology, 2003, vol. 42 (3), pp. 558-567.
Verbeek X.A., et al., "Quantification of Interventricular Asynchrony during LBBB and Ventricular Pacing," American Journal of Physiology—Heart and Circulatory Physiology, 2002, vol. 283 (4), pp. H1370-H1378.
Whinnett Z.I., et al., "Haemodynannic Effects of Changes in Atrioventricular and Interventricular Delay in Cardiac Resynchronization Therapy Show a Consistent Pattern: Analysis of Shape, Magnitude and Relative Importance of Atrioventricular and Interventricular Delay," Heart, 2006, vol. 92 (11), pp. 1628-1634.

(56) References Cited

OTHER PUBLICATIONS

Willems R., et al., "Different Patterns of Angiotensin II and Atrial Natriuretic Peptide Secretion in a Sheep Model of Atrial Fibrillation," Journal of the Cardiovascular Electrophysiology, 2001, vol. 12 (12), pp. 1387-1392.
Zupan I., et al., "Effects of Systolic Atrial Function on Plasma Renin Activity and Natriuretic Peptide Secretion after High Rate Atrial and Ventricular Pacing in Dogs," Pacing and Clinical Electrophysiology, 2005, vol. 28 (Supp 1), pp. S270-S274.
Office Action dated Jan. 29, 2015 in U.S. Appl. No. 13/688,978.
Office Action dated May 4, 2015 in U.S. Appl. No. 13/854,283.
Office Action dated Jun. 4, 2015 in U.S. Appl. No. 13/957,499.
Office Action dated Jun. 10, 2015 in U.S. Appl. No. 13/960,015.
Office Action dated Jul. 13, 2015 in U.S. Appl. No. 14/642,952.
Office Action dated Aug. 14, 2015 in U.S. Appl. No. 13/688,978.
Amendment filed Oct. 9, 2015 in U.S. Appl. No. 14/642,952.
Amendment filed Oct. 16, 2015 in U.S. Appl. No. 13/854,283.
Amendment filed Nov. 5, 2015 in U.S. Appl. No. 13/688,978.
Office Action dated Nov. 4, 2015 in U.S. Appl. No. 14/427,478.
Amendment filed Nov. 30, 2015 in U.S. Appl. No. 13/957,499.
Amendment filed Dec. 3, 2015 in U.S. Appl. No. 13/960,015.
Notice of Allowance dated Dec. 18, 2015 in U.S. Appl. No. 13/854,283.
Notice of Allowance dated Jan. 8, 2016 in U.S. Appl. No. 14/642,952.
Amendment filed Jan. 13, 2016 in U.S. Appl. No. 14/427,478.
Final Office Action dated Jan. 20, 2016 in U.S. Appl. No. 13/960,015.
Notice of Allowance dated Feb. 12, 2016 in U.S. Appl. No. 13/688,978.
Notice of Allowance dated Feb. 12, 2016 in U.S. Appl. No. 14/427,478.
Office Action dated May 27, 2016 in European Patent Application No. 13826807.3.
Amendment filed Apr. 7, 2016 in U.S. Appl. No. 13/960,015.
Notice of Allowance dated Apr. 13, 2016 in U.S. Appl. No. 13/957,499.
Advisory Action dated Apr. 18, 2016 in U.S. Appl. No. 13/960,015.
Klabunde, Richard E., "Determinants of Myocardial Oxygen Consumption," Cardiovascular Physiology Concepts, Apr. 2, 2007, retrieved Oct. 7, 2016 from: <URL: https://web.archive.org/web/20070403052549/http://www.cvphysiology.com/CAD/CAD004.htm>, 2 pages.
Office Action dated Sep. 22, 2015 in U.S. Appl. No. 13/884,144.
Amendment filed Dec. 4, 2015 in U.S. Appl. No. 13/884,144.
Final Office Action dated Jan. 21, 2016 in U.S. Appl. No. 13/884,144.
Amendment filed Apr. 14, 2016 in U.S. Appl. No. 13/884,144.
Office Action dated Jun. 10, 2016 in U.S. Appl. No. 13/884,144.
Interview Summary dated Jul. 14, 2016 in U.S. Appl. No. 13/884,144.
Amendment filed Aug. 15, 2016 in U.S. Appl. No. 13/884,144.
Notice of Allowance dated Sep. 1, 2016 in U.S. Appl. No. 13/884,144.
Amendment filed Oct. 26, 2016 in U.S. Appl. No. 15/163,078.
PCT Notification of Transmittal of the International Search Report and the Written Opinion of the International Searching Authority; International Search Report; and Written Opinion, dated Nov. 28, 2016 in International Application No. PCT/US2016/051023.
Office Action dated Jun. 16, 2017 in U.S. Appl. No. 14/652,856.
Amendment filed Jun. 26, 2017 in U.S. Appl. No. 15/372,603.
Partial European Search Report dated Jul. 25, 2017 in European Patent Application No. 17169068.8.
Extended European Search Report dated Jul. 25, 2017 in European Patent Application No. 14871226.8.
PCT Invitation to Pay Additional Fees mailed Aug. 3, 2017 in International Application No. PCT/US2017/028715.
Office Action dated Aug. 11, 2017 in European Patent Application No. 14871226.8.
Notice of Allowance dated Sep. 11, 2017 in U.S. Appl. 15/372,603.
Amendment filed Jun. 6, 2016 in U.S. Appl. No. 13/960,015.
Office Action dated Jun. 28, 2016 in U.S. Appl. No. 15/143,742.
Office Action dated Jul. 21, 2016 in U.S. Appl. No. 13/960,015.
Office Action dated Jul. 27, 2016 in U.S. Appl. No. 15/163,078.
Amendment filed Sep. 27, 2016 in U.S. Appl. No. 15/143,742.

Office Action dated Sep. 5, 2016 in Chinese Patent Application No. 201380072479.3, and English translation thereof.
Response to Office Action filed Sep. 27, 2016 in European Patent Application No. 13826807.3.
Notice of Intention to Grant dated Jan. 3, 2017 in European Patent Application No. 13826807.3.
Notice of Allowance dated Jan. 18, 2017 in U.S. App. No. 15/143,742.
Amendment filed Jan. 19, 2017 in U.S. Appl. No. 13/960,015.
Response to Office Action filed Jan. 19. 2017 in Chinese Patent Application No. 201380072479.3, and English translation thereof.
Notice of Allowance dated Feb. 22, 2017 in U.S. Appl. No. 13/960,015.
Response to Restriction and Election of Species Requirement filed Dec. 8, 2017 in U.S. Appl. No. 15/092,737.
Office Action dated Dec. 27, 2017 in U.S. Appl. No. 15/092,737.
Amendment and Declaration Under 37 CFR 1.132 filed Jan. 22, 2018 in U.S. Appl. No. 15/628,870.
Amendment filed Jan. 26, 2018 in U.S. Appl. No. 15/589,134.
Notice of Allowance dated Dec. 6, 2017 in U.S. Appl. No. 14/652,856.
Supplemental Notice of Allowance dated Jan. 29, 2018 in U.S. Appl. No. 14/652,856.
Extended European Search Report dated Nov. 3, 2017 in European Patent Application No. 17169068.8.
Amendment filed Sep. 18, 2017 in U.S. Appl. No. 14/652,856.
Office Action dated Sep. 21, 2017 in U.S. Appl. No. 15/628,870.
Office Action dated Sep. 27, 2017 in U.S. Appl. No. 15/589,134.
International Search Report and Written Opinion dated Oct. 3, 2017 in International Application No. PCT/US2017/028715.
Chaliki, HP et al.; "Pulmonary Venous Pressure: Relationship to Pulmonary Artery, Pulmonary Wedge, and Left Atrial Pressure in Normal, Lightly Sedated Dogs"; Catheterization and Cardiovascular Interventions; vol. 56, Issue 3; Jun. 17, 2002; p. 432, Abstract.
Office Action dated Oct. 19, 2017 in Japanese Patent Application No. 2015-549718, and English translation thereof.
Restriction and Election of Species Requirement dated Oct. 20, 2017 in U.S. Appl. No. 15/092,737.
Office Action dated Nov. 6, 2017 in Australian Patent Application No. 2013361318.
Notice of Acceptance dated May 7, 2018 in Australian Patent Application No. 2013361318.
Notice of Intention to Grant dated May 7, 2018 in European Patent Application No. 14871226.8.
Office Action dated May 10, 2018 in Japanese Patent Application No. 2016-539929, and English translation thereof.
Office Action dated Feb. 24, 2018 in Chinese Patent Application No. 201480075987.1, and English translation thereof.
Notification Concerning Transmittal of International Preliminary Report on Patentability (IPRP) dated Mar. 22, 2018 in International Application No. PCT/US2016/051023.
Response to Examination Report filed Apr. 23, 2018 in Australian Patent Application No. 2013361318.
Amendment filed Apr. 24, 2018 in U.S. Appl. No. 15/092,737.
Notice of Allowance dated May 2, 2018 in U.S. Appl. No. 15/589,134.
Office Action dated May 16, 2018 in U.S. Appl. No. 15/628,870.
Office Action dated May 16, 2018 in U.S. Appl. No. 15/851,787.
Response to Extended European Search Report filed May 25, 2018 in European Patent Application No. 17 169 068.8.
Response to Office Action filed Jul. 11, 2018 in Chinese Patent Application No. 201480075987.1, and English machine translation thereof.
Response to Office Action filed Feb. 7, 2018 in European Patent Application No. 14871226.8.
Response to Office Action filed Mar. 28, 2018 in Japanese Patent Application No. 2015-549718, with machine English translation of Remarks and English translation of Amended Claims.
Interview Summary dated Apr. 3, 2018 in U.S. Appl. No. 15/092,737.
Office Action dated Aug. 9, 2018 in U.S. Appl. No. 15/911,249.
Response to Office Action filed Aug. 13, 2018 in U.S. Appl. No. 15/628,870.
Amendment filed Aug. 13, 2018 in U.S. Appl. No. 15/851,787.
Restriction Requirement dated Sep. 24, 2018 in U.S. Appl. No, 15/226,056.

(56) References Cited

OTHER PUBLICATIONS

Response to Final Office Action filed Oct. 24, 2018 in Japanese Patent Application No. 2015-549718, with English Translation of Amended Claims and English Machine Translation of Remarks.
Notice of Allowance dated Oct. 29, 2018 in U.S. Appl. No. 15/092,737.
Response to Office Action filed Oct. 29, 2018 in Japanese Patent Application No. 2016-539929, with English Translation of Amended Claims and English Machine Translation of Remarks.
Notice of Allowance dated Oct. 31, 2018 in U.S. Appl. No. 15/851,787.
Restriction Requirement dated Nov. 1, 2018 in U.S. Appl. No. 15/492,802.
Final Office Action dated Aug. 28, 2018 in Japanese Patent No. 2015-549718, and English translation thereof.
Notification Concerning Transmittal of International Preliminary Report on Patentability (IPRP) dated Nov. 1, 2018 in International Application No. PCT/2017/028715.
Notice of Allowance dated Nov. 26, 2018 in U.S. Appl. No. 15/628,870.
Amendment and Response to Restriction Requirement filed Nov. 26, 2018 in U.S. Appl. No. 15/226,056.
Interview Summary dated Dec. 12, 2018 in U.S. Appl. No. 15/911,249.
Response to Restriction Requirement filed Dec. 19, 2018 in U.S. Appl. No. 15/492,802.
Office Action dated Dec. 27, 2018 in U.S. Appl. No. 16/124,283.
Amendment filed Jan. 9, 2019 in U.S. Appl. No. 15/911,249.
Office Action dated Jan. 11, 2019 in U.S. Appl. No. 15/226,056.
Decision to Grant a Patent dated Dec. 6, 2018 in Japanese Patent Application No. 2016-539929, with English translation thereof.
First Examination Report dated Dec. 12, 2018 in Australian Patent Application No. 2014367229.
Response to Examination Report filed Feb. 22, 2019 in Australian Patent Application No. 2014367229.
Office Action dated Mar. 18, 2019 in U.S. Appl. No. 15/492,802.
Notice of Allowance dated Mar. 19, 2019 in U.S. Appl. No. 15/613,344.
Response to Office Action filed Mar. 27, 2019 in U.S. Appl. No. 16/124,283.
Office Action dated Apr. 8, 2019 in U.S. Appl. No. 15/911,249.
Amendment filed Apr. 10, 2019 in U.S. Appl. No. 15/226,056.
Extended European Search Report issued Jan. 21, 2019 in European Patent Application No. 16205392.6.
Decision to Grant a Patent dated Mar. 7, 2019 in Japanese Patent Application No. 2015-549718, and English translation thereof.
Notice of Acceptance dated Mar. 22, 2019 in Australian Patent Application No. 2014367229.
Extended European Search Report dated Mar. 27, 2019 in European Patent Application Number 16845150.8.

* cited by examiner

METHODS AND SYSTEMS FOR TREATING CARDIAC MALFUNCTION

This application claims the benefit of U.S. Provisional Application No. 62/217,299, filed Sep. 11, 2015, which is herein incorporated by reference in its entirety.

BACKGROUND

The present embodiments relate to the field of treating cardiac malfunction, and more particularly, to methods and systems for stimulating the heart to treat cardiac malfunction, such as congestive heart failure.

SUMMARY

Methods and systems for treating cardiac malfunction are disclosed.

In one aspect, a method for treating cardiac malfunction may include delivering a stimulation pattern of stimulation pulses to at least one cardiac chamber of a heart. At least one of the stimulation pulses may have a first stimulation setting configured to reduce at least one of end systolic volume (ESV) and end diastolic volume (EDV) in the heart, and at least one of the stimulation pulses may have a second stimulation setting different from the first stimulation setting. The stimulation pattern may be configured to reduce the at least one of end systolic volume (ESV) and end diastolic volume (EDV) by at least 5% and to maintain the at least one of end systolic volume (ESV) and end diastolic volume (EDV) on average at such reduced volume for a time period of at least one hour.

In another aspect, a system for treating cardiac malfunction may include a stimulation circuit and at least one controller. The stimulation circuit may be configured to deliver a stimulation pulse to at least one cardiac chamber of a heart of a patient. The at least one controller may be configured to execute delivery of a stimulation pattern of stimulation pulses to the at least one cardiac chamber. At least one of the stimulation pulses may have a first stimulation setting configured to reduce at least one of end systolic volume (ESV) and end diastolic volume (EDV) in the heart, and at least one of the stimulation pulses may have a second stimulation setting different from the first stimulation setting. The stimulation pattern may be configured to reduce the at least one of end systolic volume (ESV) and end diastolic volume (EDV) by at least 5% and maintain the at least one of the end systolic volume (ESV) and end diastolic volume (EDV) on average at such reduced volume for a time period of at least one hour.

Other systems, methods, features, and advantages of the present embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

A healthy cardiac contraction cycle includes two phases: a systole and a diastole. The systole is a period of cardiac contraction, commencing with ventricular contraction. The systole causes blood to be ejected from the heart and into the vascular system. At the end of this contraction, cardiac muscles relax. This period of relaxation is the diastole. During diastole, the heart passively fills with blood from the vascular system and at the end of diastole the atria contract and provide additional filling to the ventricle. Accordingly, at the end of the diastole and just before the heart begins to contract, cardiac blood volume peaks. This peak volume is the end diastolic volume (EDV). At the end of the systole, when contraction ends and cardiac filling is about to commence, cardiac blood volume reaches a minimal value. This minimal volume is the end systolic volume (ESV). The amount of blood ejected in a heartbeat is known as the stroke volume (SV) and equals the difference between end diastolic volume (EDV) and end systolic volume (ESV). The ejection fraction (EF) is the fraction of blood that is ejected by the heart (i.e., SV divided by EDV).

Cardiac remodeling is a phenomenon that results from cardiac load or injury, and is an accepted determinant of the clinical course of heart failure (HF). It manifests clinically as changes in size, shape, and function of the heart.

As a result of damage to the heart, abnormal strain patterns are manifested in the heart, and the cells that experience a high strain undergo hypertrophy and some loss of function. This affects cardiac function and blood pressure parameters, and as a consequence, neuronal and/or hormonal pathways are activated in an attempt to compensate for cardiac damage. For example, poor contraction results in high end systolic volume (ESV) and thus a reduction in stroke volume (SV). This may lead to increase in end diastolic volume (EDV) as well. As cardiac volumes increase, so does the wall tension in the heart, as known from Laplace's Law. According to the law, a dilated ventricle requires more tension in the wall to generate the same pressure as would a smaller ventricle. This increase in tension increases sympathetic stimulation and vasopressin (antidiuretic hormone or ADH) secretion. Vasopressin is known to constrict blood vessels and increase heart rate, which causes an increase in blood pressure and an increase in oxygen consumption by the heart muscle cells. However, this also causes an additional increase in cardiac strain, since the heart beats faster and in every systole needs to eject blood against a system showing an increased resistance. This increased strain may cause additional hypertrophy and further loss of function. Thus, a vicious cycle comes into play where the cardiovascular system's attempts at reducing the effect of the damaged tissue cause additional reduction in cardiac performance.

Many attempts have been made to develop devices and methods to treat heart failure, including, for example, devices intended to mechanically control cardiac volumes:

U.S. Pat. No. 7,651,461 to Alferness et al., entitled "Cardiac Support with Metallic Structure," which is herein incorporated by reference in its entirety, describes a jacket "configured to surround the myocardium" which "provides reduced expansion of the heart wall during diastole by applying constraining surfaces at least at diametrically opposing aspects of the heart;" and U.S. Pat. No. 7,618,364 to Walsh et al., entitled "Cardiac Wall Tension Relief Device and Method," which is herein incorporated by reference in its entirety, states that "[i]t is believed that such resistance decreases wall tension on the heart and permits a diseased heart to beneficially remodel."

Interfering with cardiac filling may reduce blood pressure in hypertensive patients. One option for interfering with cardiac filling to reduce blood pressure may be to reduce or even eliminate atrial kick. Atrial kick may provide a relatively small boost to ventricle filling (10-30%) that is caused by atrial contraction before an atrioventricular (AV) valve between the atrium and the ventricle is closed. Once the ventricle begins to contract, pressure builds up in the ventricle and causes the AV valve to passively close. The inventors also found that when effecting treatment that reduces or even eliminates atrial kick, the cardiovascular system acts to adapt to the change and return performance values to those that occurred before treatment commenced. International Publications Nos. WO2015/094401 and WO2014/100429, both to Mika et al., and both herein incorporated by reference in their entirety, describe, inter alia, methods and systems providing pacing patterns of stimulation pulses that comprise pulses configured to reduce or prevent atrial kick and also reduce or even eliminate the cardiovascular system's adaptation to the reduction in blood pressure. The reduction in adaptation may be achieved by reducing neurohormonal response to changes in generated pressure and stretch using specific patterns.

Heart failure patients, on the other hand, typically (although not exclusively) have blood pressure values that are not significantly elevated. Accordingly, in some cases, it may be preferred to reduce cardiac volumes (e.g., at least one of end diastolic volume and end systolic volume) and/or reduce cardiac strain without significantly affecting blood pressure.

The inventors have developed methods and systems of applying cardiac stimulations that yield surprising results in meeting the needs of heart failure patients. Embodiments provide methods and system that may reduce the strain sensed by cardiac muscles by applying cardiac stimulations that reduce at least one of end systolic volume (ESV) and end diastolic volume (EDV) without significantly affecting the ejection fraction (EF) of the heart, and optionally also without significantly affecting blood pressure. A reduction of such strain may be useful in reversing cardiac remodeling or at least in slowing down or even stopping the remodeling process. In some embodiments, a stimulation pattern may be configured to reduce a neurohormonal response to changes in strain without significantly affecting blood pressure.

Optionally, when a patient is provided with a cardiac stimulation device, a stimulation pattern is selected based on sensing of one or more of: at least one blood-pressure-related parameter (e.g., an indication of pretreatment and/or treatment blood pressure) and at least one cardiac-strain and/or volume-related parameter (e.g., a pressure measurement within a chamber and/or echocardiogram-derived information). These parameters can be used to adjust one or more of the properties of one or more (or two or more) pulses in a pulse pattern and/or the proportion between pulses having different settings and/or the order of the pulses in the pattern. Optionally, reducing at least one of end diastolic volume (EDV) and end systolic volume (ESV) suppresses sympathetic stimulation, for example, by at least one of reducing wall strain and hence reducing or eliminating the activation of sympathetic pathways involved with adaptation of the cardiovascular system to changes.

Optionally, a device is configured to receive feedback information regarding one or more of the at least one blood-pressure-related parameter and at least one cardiac strain/volume related parameter. This may be performed periodically (e.g., in a periodic measurement such as a periodic checkup) and/or ongoing (e.g., with an associated or integral sensor). The information may be received, for example, via communication with a user through an input interface and/or by communication with implanted and/or external devices. Further details of suitable devices are described below in reference to FIG. 8.

A stimulation setting means one or more parameters of one or more stimulation pulses delivered in a single cardiac cycle. For example, these parameters may include one or more of: a time interval between electrical pulses that are included in a single stimulation pulse (e.g., AV delay), a period of delivery with respect to the natural rhythm of the heart, the length of a stimulation pulse or a portion thereof, and the site of delivery between two or more chambers. In some embodiments, a pulse setting includes applying an excitatory pulse to a ventricle, timed in synchronization to the natural activity of an atrium of the heart. In some embodiments, a pulse setting includes applying an excitatory pulse to an atrium timed in synchronization to the natural activity of a ventricle of the heart. In some embodiments, a pulse setting includes applying an excitatory pulse to each of a ventricle and an atrium.

A stimulation pattern may include a series of pulses having identical stimulation settings or a stimulation pattern may include multiple pulses each having different stimulation settings. For example, a stimulation pattern may have one or more pulses having a first setting and one or more pulses having a second setting that is different from the first setting. When stating that a stimulation pattern has a setting, it is understood that this means a stimulation pattern may include at least one stimulation pulse having that setting. It is also understood that, in some embodiments a stimulation pattern may include one or more cardiac cycles where no stimulation pulse is delivered, in which case the pulse(s) may be viewed as being delivered at zero power. A stimulation pattern may include a plurality of identical pulses or a sequence of pulses including two or more different settings. Two stimulation sequences in a pattern may differ in the order of pulses provided within a setting. Two or more stimulation sequences may optionally differ in their lengths (in time and/or number of heartbeats). In some embodiments, a stimulation pattern may include pulses having blood pressure reduction (BPR) settings. In some embodiments, a stimulation pattern may include pulses that do not have BPR settings.

Experimental Results

In an experiment according to a first embodiment, a plurality of patients' hearts were paced at the ventricle and atrium using a pacing pattern that included 9 to 10 pulses having a first stimulation setting (according to which the ventricle was stimulated 40-90 milliseconds after atrial activation) and 1 to 2 pulses having a second stimulation setting (according to which the ventricle was stimulated 100-180 milliseconds after atrial activation). Pulses having the first stimulation setting reduced atrial kick, while pulses having the second stimulation setting did not do so. The pacing pattern was applied continuously for a period of up to about six months. Changes in end systolic volume (ESV), end diastolic volume (EDV), and ejection fraction (EF) were derived from echocardiogram data.

Figure 1:
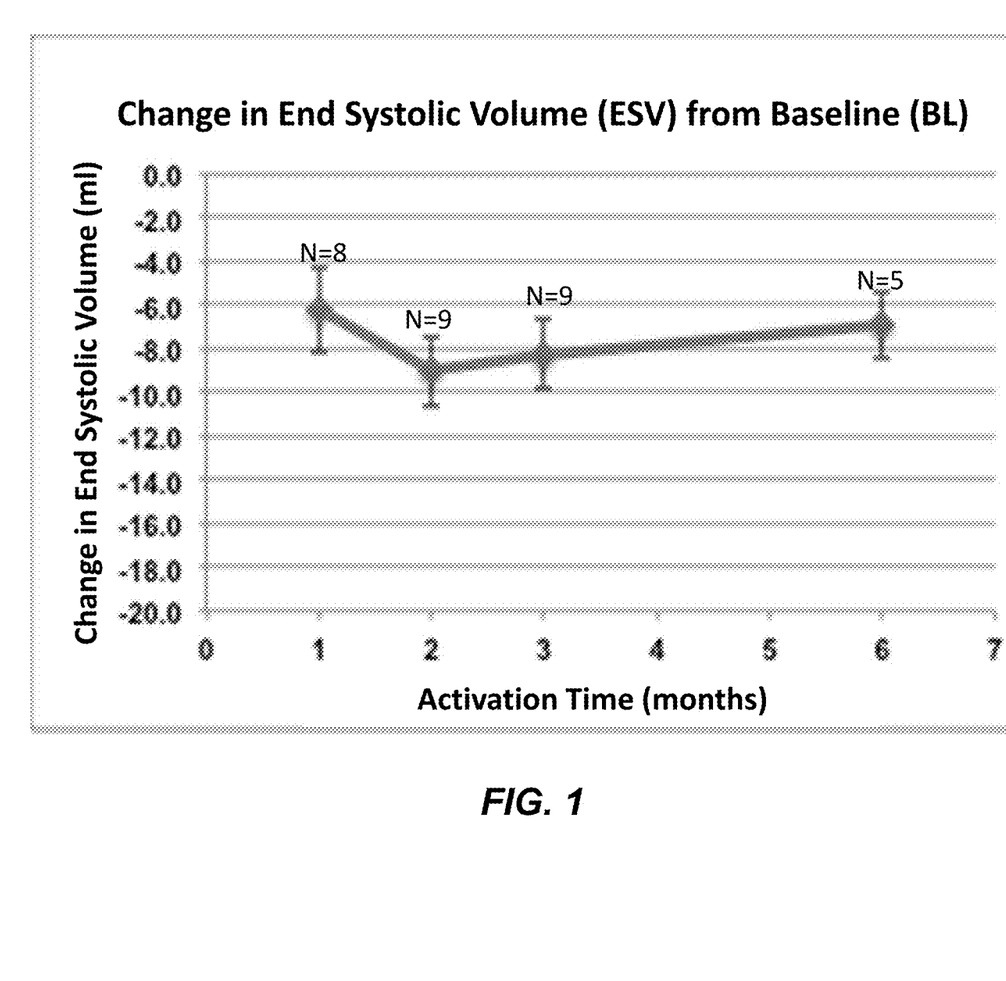
FIG. 1 is a plot illustrating change in end systolic volume (ESV) from baseline (BL) as a function of activation time, according to an embodiment.
Figure 2:
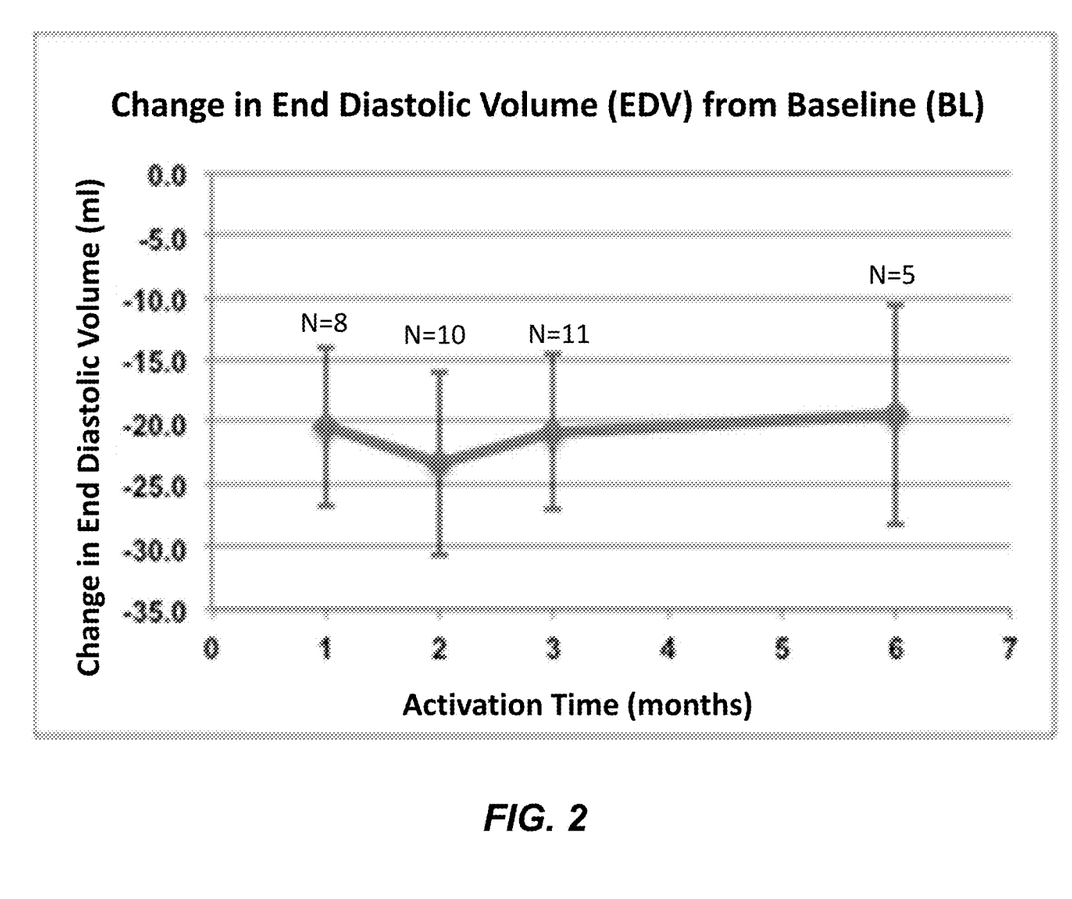
FIG. 2 is a plot illustrating change in end diastolic volume (EDV) from baseline (BL) as a function of activation time, according to an embodiment.
Figure 3:
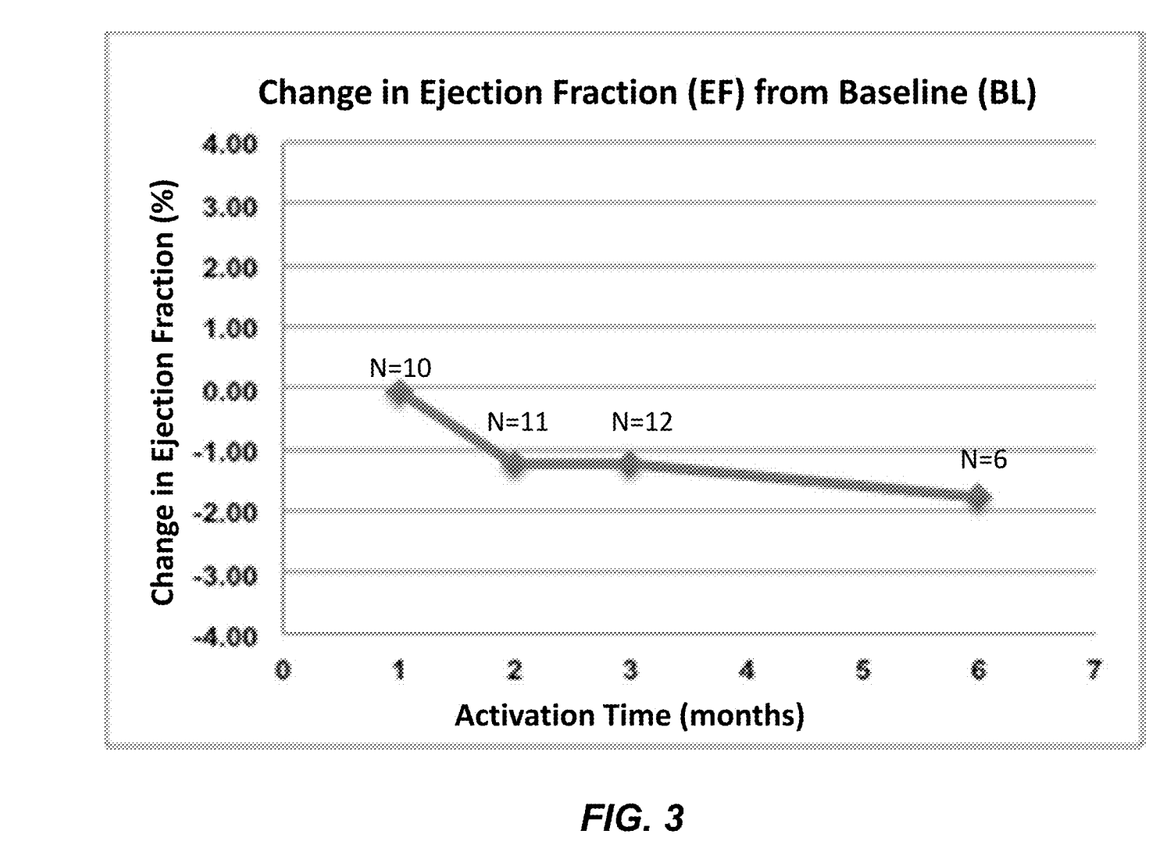
FIG. 3 is a plot illustrating change in ejection fraction (EF) from baseline (BL) as a function of activation time, according to an embodiment.

Before treatment, end systolic volume (ESV) and end diastolic volume (EDV) were measured and ejection fraction (EF) was calculated to provide baseline (BL) values for each patient. Thereafter, the same values were obtained approximately one, two, three, and six months after treatment commenced, and the change from baseline (BL) for each patient was calculated. Each of FIGS. 1-3 depicts results obtained for a plurality of patients (N), as indicated on the plots. The numbers (N) of patients includes only data for which a core lab analysis determined that the echocardiogram was suitable for measurement. The baseline values were approximately 110 ml for diastolic volume, approximately 45 ml for systolic volume, and approximately 62% for ejection fraction.

As shown in FIGS. 1-3, for a period of up to about six months, end systolic volume (ESV) decreased by approximately 7 ml (about 15%), end diastolic volume (EDV) decreased by approximately 20 ml (about 17%), and ejection fraction (EF) decreased slightly (about a 2% decrease). This means that muscle strain was reduced (due to the lower volume of blood in the chambers), while the heart's efficiency (as shown by the ejection fraction (EF)) remained almost unchanged. A reduction of strain works against the vicious cycle of the heart in which cardiac strain plays a significant role, especially when ejection fraction (EF) is not significantly reduced, and thus remodeling is prevented or at least its progress rate is reduced. Experimental observations suggest that beneficial effects may be obtained over a shorter period, for example, reducing at least one of end systolic volume (ESV) and end diastolic volume (EDV) by at least 5% and maintaining the at least one of end systolic volume (ESV) and end diastolic volume (EDV) on average at such reduced volume for a time period of at least one hour. In particular, according to Laplace's Law, pressure (P) is directly proportional to wall tension (T) and inversely proportional to radius (R), such that $P \propto T/R$. This means that, as long as pressure (P) is maintained essentially constant, wall tension (T) is a direct function of radius (R). Cardiac volume (V) in turn is a function of $R^3$, so T is a direct function of $V^{1/3}$. Therefore, when V decreases by approximately 20%, R decreases by approximately 7%, and so does T. In other words, a 20% decrease in V is $(0.8 \times V)$, and $(0.8)^{1/3}$ equals 0.93, yielding $(0.93 \times R)$, or a 0.07 (or 7%) decrease in R. Extending this analysis to the at least 5% reduction suggested by the experimental observations, when V decreases by approximately 5%, R decreases by approximately 2%, and so does T.

Figure 4:
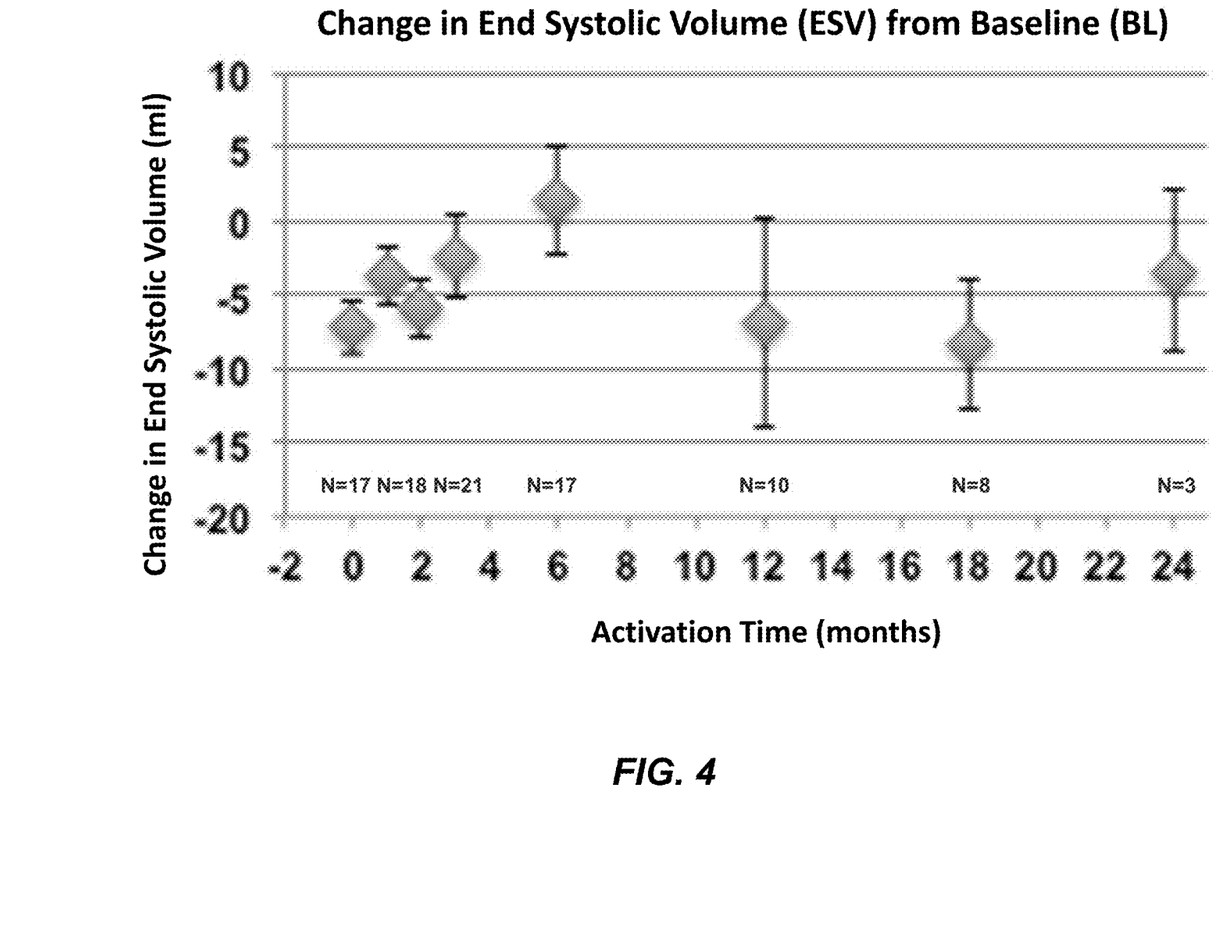
FIG. 4 is a plot illustrating change in end systolic volume (ESV) from baseline (BL) as a function of activation time over a longer period (about twenty-four months), according to a second embodiment.
Figure 5:
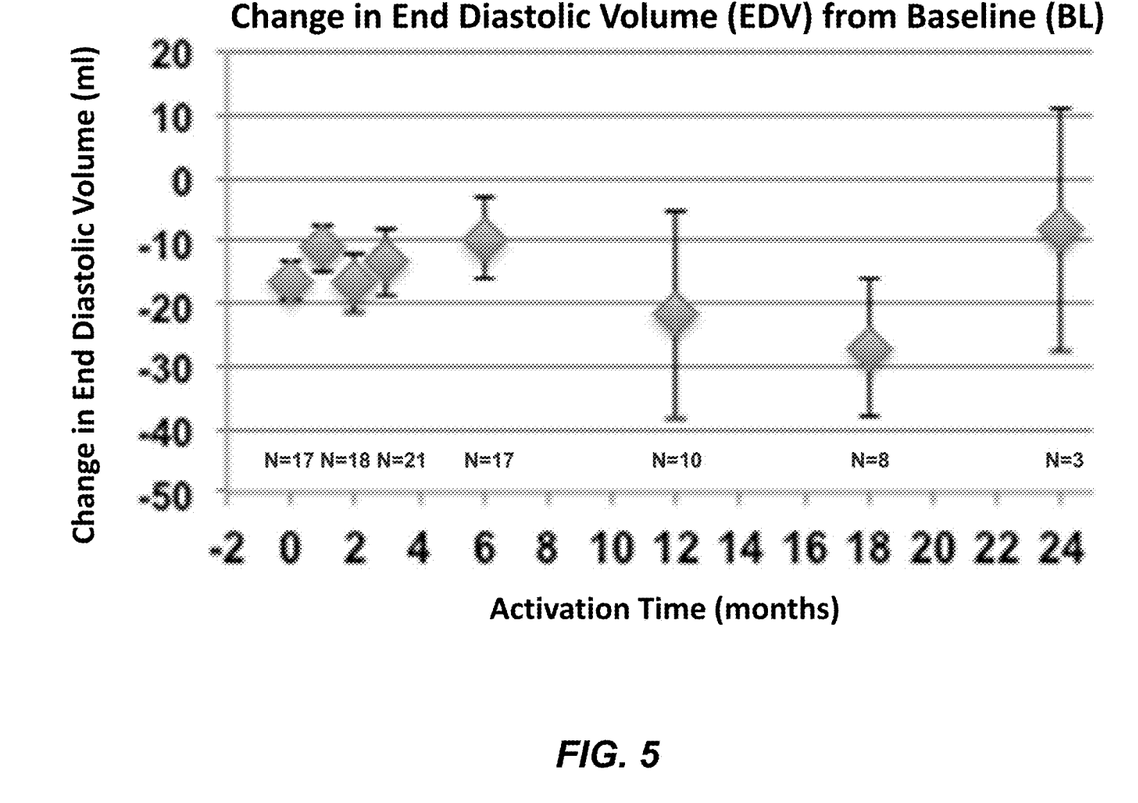
FIG. 5 a plot illustrating change in end diastolic volume (EDV) from baseline (BL) as a function of activation time over the longer period (about twenty-four months), according to the second embodiment.
Figure 6:
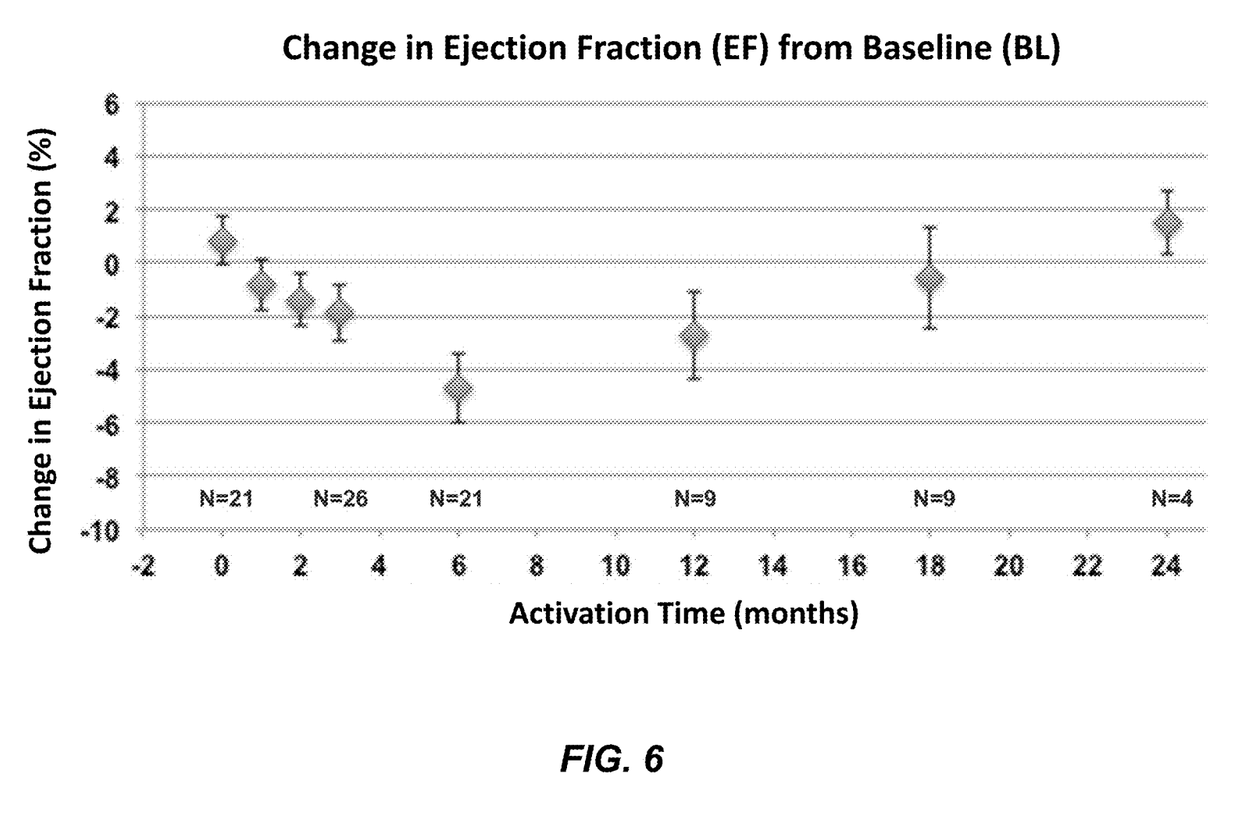
FIG. 6 is a plot illustrating change in ejection fraction (EF) from baseline (BL) as a function of activation time over the longer period (about twenty-four months), according to the second embodiment.

FIGS. 4-6 illustrate a second set of experimental results according to a second embodiment, over a longer period of activation time (about twenty-four months), and including a greater number of patients. Similar to the first embodiment, in the experiment of the second embodiment, a plurality of patients' hearts were paced at the ventricle and atrium using a pacing pattern that included 9 to 10 pulses having a first stimulation setting (according to which the ventricle was stimulated 40-90 milliseconds after atrial activation) and 1 to 2 pulses having a second stimulation setting (according to which the ventricle was stimulated 100-180 milliseconds after atrial activation). Pulses having the first stimulation setting reduced atrial kick, while pulses having the second stimulation setting did not do so. The pacing pattern was applied continuously for a period of up to about twenty-four months. Changes in end systolic volume (ESV), end diastolic volume (EDV), and ejection fraction (EF) were derived from echocardiogram data.

Before treatment, end systolic volume (ESV) and end diastolic volume (EDV) were measured and ejection fraction (EF) was calculated to provide baseline (BL) values for each patient. Thereafter, the same values were obtained eight times after treatment commenced, and the change from baseline (BL) for each patient was calculated. The eight times were at approximately the following months after treatment commenced: one, two, three, six, twelve, eighteen, and twenty-four. Each of FIGS. 4-6 depicts results obtained for a plurality of patients (N), as indicated on the plots. The numbers (N) of patients includes only data for which a core lab analysis determined that the echocardiogram was suitable for measurement. The baseline values were approximately 115 ml for diastolic volume and approximately 40 ml for systolic volume.

As shown in FIGS. 4-6, for a period of up to about twenty-four months, end systolic volume (ESV) and end diastolic volume (EDV) remained at reduced levels, with values at the twenty-four month decreased by about 9% and 8%, respectively, while ejection fraction (EF) initially decreased slightly and insignificantly, and later increased steadily (to about a 2% increase at twenty-four months). This means that muscle strain was reduced (due to the lower volume of blood in the chambers), while the heart's efficiency (as shown by the ejection fraction (EF)) improved slightly. A reduction of strain works against the vicious cycle of the heart in which cardiac strain plays a significant role, especially when ejection fraction (EF) improves, and thus remodeling is prevented or at least its progress rate is reduced. The longer term data of FIGS. 4-6 therefore demonstrates a slight increase in ejection fraction (~60%) with normal global cardiac function over a period of twenty-four months, which suggests a trend toward continuing improvement of cardiac function beyond that longer term. Thus, in embodiments, a stimulation pattern may be configured to reduce the at least one of end systolic volume (ESV) and end diastolic volume (EDV) by at least 5% and maintain the at least one of end systolic volume (ESV) and end diastolic volume (EDV) on average at such reduced volume for a time period of at least one hour, including as long as three months, twenty-four months, or even longer.

In light of the experimental results, embodiments provide methods and systems for treating cardiac malfunction. In a first aspect, a method for treating cardiac malfunction may include delivering a stimulation pattern of stimulation pulses to at least one cardiac chamber of a heart. At least one of the stimulation pulses may have a first stimulation setting configured to reduce at least one of end systolic volume (ESV) and end diastolic volume (EDV) in the heart and at least one of the stimulation pulses may have a second stimulation setting different from the first stimulation setting. The stimulation pattern may be configured to reduce the at least one of end systolic volume (ESV) and end diastolic volume (EDV) by at least 5% and maintain the at least one of end systolic volume (ESV) and end diastolic volume (EDV) on average at such reduced volume for a time period of at least one hour.

Figure 7:
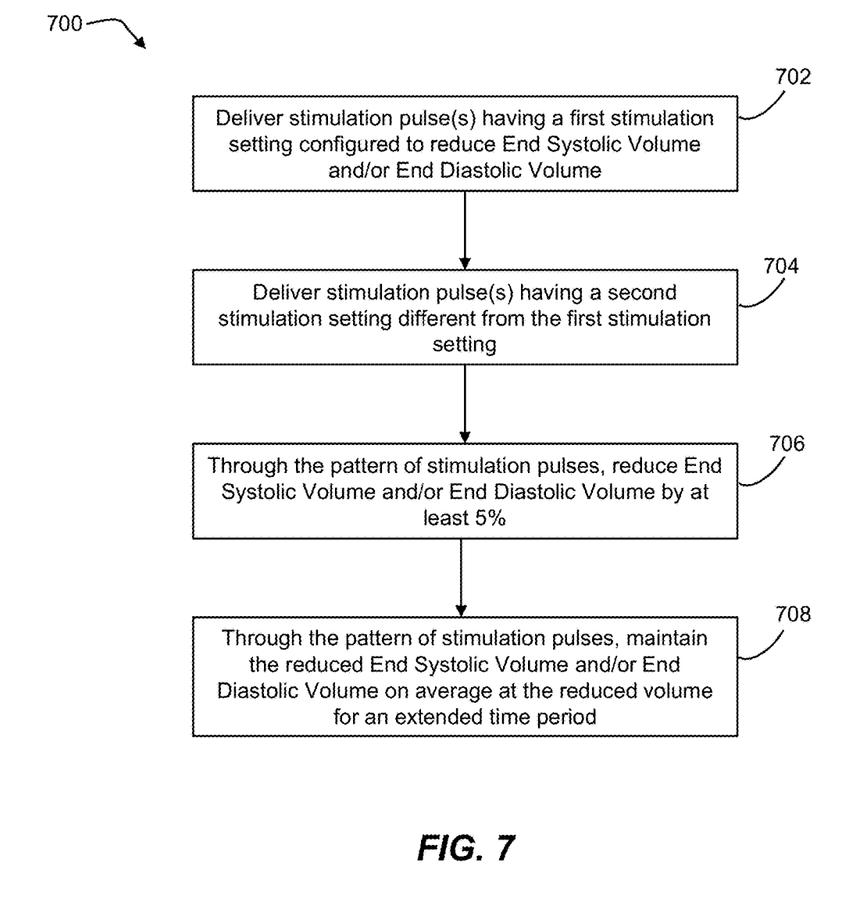
FIG. 7 is a flow chart illustrating an exemplary method for treating cardiac malfunction, according to an embodiment.

FIG. 7 illustrates an embodiment of the first aspect, providing a method 700 for treating cardiac malfunction that includes delivering a stimulation pattern of stimulation pulses to at least one cardiac chamber of a heart. As shown, in step 702, the method may begin by delivering at least one stimulation pulse having a first stimulation setting configured to reduce at least one of end systolic volume (ESV) and end diastolic volume (EDV) in the heart. In step 704, the method may continue by delivering at least one stimulation pulse having a second stimulation setting different from the first stimulation setting. Through the delivery of the stimulation pattern of stimulation pulses of steps 702 and 704, the method in step 706 reduces end systolic volume (ESV) and/or end diastolic volume (EDV) by at least 5% and in step 708 maintains the reduced end systolic volume (ESV) and/or end diastolic volume (EDV) on average at such reduced volume for an extended time period (e.g., at least one hour).

In a second aspect, the time period may be at least three months.

In a third aspect, the method of the first or second aspect may include a stimulation pattern configured to reduce cardiac strain by at least 2% and maintain the cardiac strain on average at such reduced strain for the time period.

In a fourth aspect, the method of any of the preceding aspects may include a stimulation pattern configured to maintain blood pressure within an average pressure of ±10% as compared to a pretreatment blood pressure value for the time period.

In a fifth aspect, the method of any of the preceding aspects may include a stimulation pattern configured to prevent cardiac remodeling in the patient.

In a sixth aspect, the method of any of the preceding aspects may provide that the first stimulation setting is configured to reduce or prevent atrial kick in at least one ventricle and at least one of the stimulation pulses has a second stimulation setting different from the first stimulation setting.

In a seventh aspect, the method of any of the preceding aspects may provide that the first stimulation setting is configured to reduce the at least one of end systolic volume (ESV) and end diastolic volume (EDV) by at least 5% and the second stimulation setting is configured to reduce a baroreflex response or adaptation to the reduction in the at least one of end systolic volume (ESV) and end diastolic volume (EDV). In some embodiments, the stimulation pattern is configured not to activate a baroreceptor of the patient.

In an eighth aspect, the method of any of the preceding aspects may provide that the stimulation pattern is configured to reduce a baroreflex response or adaptation to the reduction in the at least one of end systolic volume (ESV) and end diastolic volume (EDV).

In a ninth aspect, the method of any of the preceding aspects may provide that the first stimulation setting is configured to reduce the at least one of end systolic volume (ESV) and end diastolic volume (EDV) by at least 5% and the second stimulation setting is configured to reduce a neuronal response or adaptation to the reduction in the at least one of end systolic volume (ESV) and end diastolic volume (EDV).

In a tenth aspect, the method of any of the preceding aspects may provide that the stimulation pattern is configured to reduce a neuronal response or adaptation to the reduction in the at least one of end systolic volume (ESV) and end diastolic volume (EDV).

In an eleventh aspect, the method of any of the preceding aspects may provide that the first stimulation setting is configured to reduce the at least one of end systolic volume (ESV) and end diastolic volume (EDV) by at least 5% and the second stimulation setting is configured to increase hormonal secretion.

In a twelfth aspect, the method of any of the preceding aspects may provide that the stimulation pattern is configured to increase hormonal secretion.

In a thirteenth aspect, the method of any of the preceding aspects may provide that the first stimulation setting comprises stimulating a ventricle of the heart 40-90 milliseconds after atrial activation.

In a fourteenth aspect, the method of the thirteenth aspect may provide that the second stimulation setting comprises stimulating an atrium of the heart to thereby produce atrial stimulation.

In a fifteenth aspect, the method of any of the preceding aspects may provide that the second stimulation setting comprises stimulating a ventricle of the heart 100-180 milliseconds after atrial activation.

In a sixteenth aspect, the method of any of the first aspect through fourteenth aspect may provide that the second stimulation setting comprises allowing a natural AV delay to occur.

In a seventeenth aspect, the method of any of the preceding aspects may provide that the stimulation pattern includes at least 4 consecutive heartbeats having the first stimulation setting for every 1 consecutive heartbeat having the second stimulation setting.

In an eighteenth aspect, the method of the seventeenth aspect may provide that the stimulation pattern includes at least 8 consecutive heartbeats having the first stimulation setting for every 1 consecutive heartbeat having the second stimulation setting.

In a nineteenth aspect, the method of any of the preceding aspects may provide that the stimulation pattern comprises at least one stimulation pulse having a third stimulation setting different from the first and second stimulation settings.

In a twentieth aspect, the method of any of the preceding aspects may provide that the cardiac malfunction is associated with an increase in at least one of end systolic volume (ESV) and end diastolic volume (EDV).

In a twenty-first aspect, the method of any of the preceding aspects may provide that the cardiac malfunction is congestive heart failure.

In a twenty-second aspect, the method of any of the preceding aspects may further include applying the stimulation pattern at a stimulation pattern configuration for a first period, sensing at least one parameter indicative of at least one of end systolic volume (ESV), end diastolic volume (EDV), cardiac strain, and blood pressure for the first period, and adjusting the stimulation pattern configuration according to the sensing.

In a twenty-third aspect, the method of the twenty-second aspect may provide that adjusting the stimulation pattern includes adjusting at least one of the first stimulation setting and the second stimulation setting.

In a twenty-fourth aspect, the method of either the twenty-second or twenty-third aspect may provide that adjusting the stimulation pattern configuration includes adjusting at least one of the number and proportion of at least one of stimulation pulses having the first stimulation setting and stimulation pulses having the second stimulation setting within the stimulation pattern.

Another aspect provides a system for treating cardiac malfunction. The system may include a stimulation circuit configured to deliver a stimulation pulse to at least one cardiac chamber of a heart of a patient, and at least one controller configured to execute delivery of a stimulation pattern of stimulation pulses to the at least one cardiac chamber. At least one of the stimulation pulses may have a first stimulation setting configured to reduce at least one of end systolic volume (ESV) and end diastolic volume (EDV) in the heart and at least one of the stimulation pulses may have a second stimulation setting different from the first stimulation setting. The stimulation pattern may be configured to reduce the at least one of end systolic volume (ESV) and end diastolic volume (EDV) by at least 5% and maintain the at least one of end systolic volume (ESV) and end diastolic volume (EDV) on average at such reduced volume for a time period of at least one hour.

In a further aspect of the system, the at least one controller may be configured to receive input data relating to at least one sensed parameter indicative of at least one of end systolic volume (ESV), end diastolic volume (EDV), cardiac strain, and blood pressure for the time period and to adjust the stimulation pattern configuration according to the at least one sensed parameter.

In a further aspect of the system, the system may further comprise at least one sensor configured to sense the at least one sensed parameter and to communicate the input data to the at least one controller.

In a further aspect of the system, the at least one controller, the stimulation circuit, and the at least one sensor may be combined in a single device.

Figure 8:
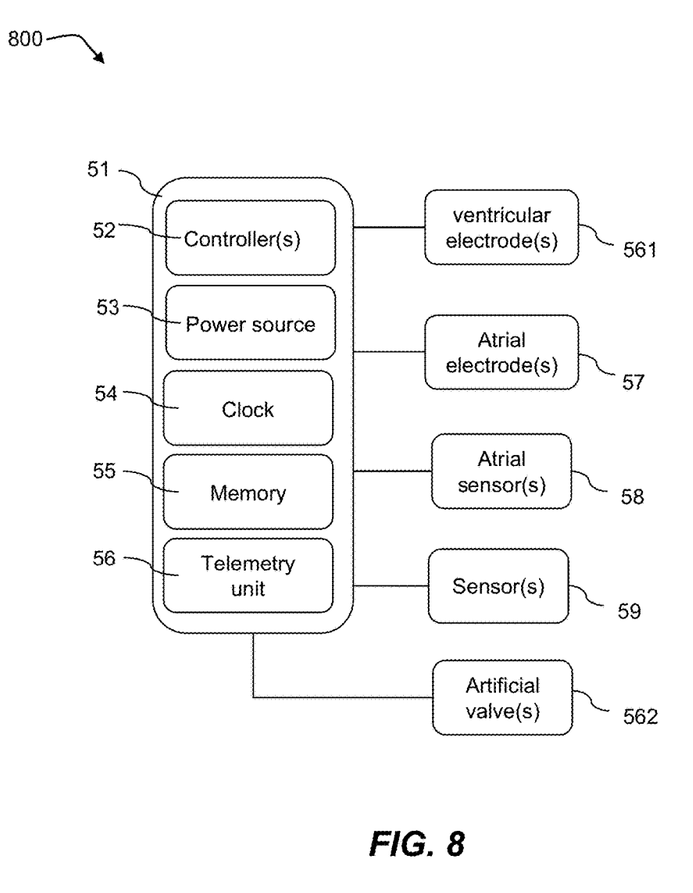
FIG. 8 is a schematic drawing illustrating an exemplary system for treating cardiac malfunction, which may perform one or more of the methods described herein, such as the method of FIG. 7.

FIG. 8 illustrates an embodiment of a system 800 for treating cardiac malfunction, which includes a stimulation circuit and at least one controller as described above. System 800 may be constructed and have components similar to a cardiac pacemaker essentially as known in the art with some modifications as discussed herein. Optionally, the system, or device, is implantable. Optionally, the system comprises components that may provide additional and/or alternative electrical treatments of the heart (e.g., defibrillation). System 800 may be configured for implantation in the body of a patient essentially as is known in the art for implantable pacemakers, optionally with some modifications as discussed herein.

System 800 may include a biocompatible body 51, one or more controllers 52, a power source 53, and a telemetry unit 56. Body 51 may comprise a housing for encasing a plurality of components of the system. Controller(s) 52 may be configured to control the operation of the system, and may implement any of the embodiments and methods disclosed herein. For example, controller(s) 52 may control the delivery of stimulation pulses. In some embodiments, power source 53 may include a battery. For example, power source 53 may include a rechargeable battery. In some embodiments, power source 53 may include a battery that is rechargeable by induction. In some embodiments, telemetry unit 56 may be configured to communicate with one or more other units and/or components. For example, telemetry unit 56 may be configured to communicate with an external programmer and/or a receiving unit for receiving data recorded on system 800 during operation.

In some embodiments, system 800 may include one or more electrodes and/or sensors. The electrodes and/or sensors may be integrated in system 800, attached thereto, and/or connectable therewith. In some embodiments, the electrodes may include ventricular electrode(s) 561 configured to pace at least one ventricle. Additionally or alternatively, the system may be connected, optionally via wires or wirelessly, to at least one implanted artificial valve 562. Additionally, system 800 may comprise one or more atrial electrode(s) 57 for pacing one or more atria, and/or one or more atrial sensors 58 for sensing the onset of atrial excitation, and/or one or more sensors 59 for providing other feedback parameters (e.g., a blood-pressure-related parameter and a cardiac strain/volume related parameter).

In some embodiments, sensor(s) 59 may comprise one or more pressure sensors, electrical sensors (e.g., ECG monitoring), flow sensors, heart rate sensors, activity sensors, and/or volume sensors. Sensor(s) 59 may include mechanical sensors and/or electronic sensors (e.g., ultrasound sensors, electrodes, and/or RF transceivers). In some embodiments, sensor(s) 59 may communicate with system 800 via telemetry.

In some embodiments, ventricular electrode(s) 561 and/or atrial electrode(s) 57 may be standard pacing electrodes. Ventricular electrode(s) 561 may be positioned relative to the heart at positions as known in the art for ventricular pacing. For example, ventricular electrode(s) may be placed in and/or near one or more of the ventricles. In some embodiments, atrial electrode(s) 57 may be placed in and/or near one or more of the atria. In some embodiments, atrial electrode(s) 57 may be attached to the one or more atria at one or more positions selected to provide early detection of atrial excitation or depolarization. For example, in some embodiments, atrial electrode(s) 57 may be attached to the right atrium near the site of the sinoatrial (SA) node.

One position of ventricular electrode(s) 561 may be such that pacing may reduce or minimize the prolongation of QRS when the heart is paced, to reduce or even minimize dyssynchrony. In some embodiments, this position is on the ventricular septum near the Bundle of His. Ventricular electrode(s) 561 may additionally or alternatively be placed on the epicardium of the heart or in coronary veins. More than one electrode can be placed on the ventricles to provide biventricular pacing, optionally to reduce dyssynchrony.

System 800 may include a pulse generator, or stimulation circuit, configured to deliver a stimulation pulse to at least one cardiac chamber. The pulse generator, or stimulation circuit, may include some or all standard capabilities of a conventional pacemaker. Controller 52 may be configured to control the pulse generator, or stimulation circuit. Atrial sensor(s) 58 (and optionally other electrode sensors configured to sense other heart chambers) may be connected to system 800 via specific circuits that amplify the electrical activity of the heart and allow sampling and detection of the activation of the specific chamber. Other circuits may be configured to deliver stimulation to a specific electrode to pace the heart, creating propagating electrical activation.

In some embodiments, one or more additional sensors 59 may be placed in and/or on one or more of the atria and/or in and/or on one or more of the ventricles and/or in and/or on one or more other locations that might optionally be adjacent the heart. For example, one or more sensors may be placed on and/or in vena cava and/or on one or more arteries and/or within one or more cardiac chambers. These sensors may measure pressure, or other indicators, such as, for example, impedance and/or flow.

In some embodiments, controller 52 may comprise or be a microprocessor powered by power source 53. In some embodiments, system 800 may comprise a clock 54, for example, generated by a crystal. System 800 may comprise an internal memory 55 and/or be connected to external memory. For example, device may connect to an external memory via telemetry unit 56. In some embodiments, telemetry unit 56 may be configured to allow communication with external devices such as a programmer and/or one or more of sensors 59. Any and all feedback information and/or a log of device operation may be stored in internal memory 55 and/or relayed by telemetry unit 56 to an external memory unit.

In some embodiments, controller 52 may operate in accordance with at least one embodiment of a method described herein.

In some embodiments, system 800 may comprise one or more sensors for sensing one or more feedback parameters to control the application of the AV delay and/or its magnitude.

According to further embodiments, additional systems and devices suitable for implementing the methods presented herein are described in U.S. Pat. No. 9,370,662 to Mika et al., issued Jun. 21, 2016, for example, in reference to FIGS. 9 and 14 of that patent. The entirety of U.S. Pat. No. 9,370,662 is herein incorporated by reference.

The foregoing disclosure has been presented for purposes of illustration and description. It is not intended to be exhaustive or to limit the embodiments to the precise forms disclosed. Many variations and modifications of the embodiments described herein will be apparent to one of ordinary skill in the art in light of the above disclosure.

While various embodiments have been described, the description is intended to be exemplary, rather than limiting and it will be apparent to those of ordinary skill in the art that many more embodiments and implementations are possible that are within the scope of the embodiments. Any feature of any embodiment may be used in combination with or substituted for any other feature or element in any other embodiment unless specifically restricted. Accordingly, the embodiments are not to be restricted except in light of the attached claims and their equivalents. Also, various modifications and changes may be made within the scope of the attached claims.

Further, in describing representative embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the present embodiments.

What is claimed is:

1. A system for treating cardiac malfunction, comprising:
   a stimulation circuit configured to deliver a stimulation pulse to at least one cardiac chamber of a heart of a patient; and
   at least one controller configured to execute delivery of a stimulation pattern of stimulation pulses to the at least one cardiac chamber over a time period of at least three months,
   wherein at least one of the stimulation pulses has a first stimulation setting configured to reduce end diastolic volume (EDV) in the heart of the patient and at least one of the stimulation pulses has a second stimulation setting different from the first stimulation setting, and
   wherein the stimulation pattern is configured to:
      reduce, during the time period of at least three months, the end diastolic volume (EDV) by at least 5%,
      maintain, during the time period of at least three months, the end diastolic volume (EDV) in the heart of the patient on average at such reduced volume, and
      maintain, during the time period of at least three months, blood pressure of the patient within an average pressure of ±10% as compared to a pretreatment blood pressure value.

2. The system of claim 1, wherein the at least one controller is configured to receive input data relating to at least one sensed parameter indicative of cardiac strain for the time period and to adjust the stimulation pattern configuration according to the at least one sensed parameter.

3. The system of claim 2, further comprising at least one sensor configured to sense the at least one sensed parameter and to communicate the input data to the at least one controller.

4. The system of claim 3, wherein the at least one controller, the stimulation circuit, and the at least one sensor are combined in a single device.

5. A method for treating cardiac malfunction, comprising:
   delivering over a time period of at least three months a stimulation pattern of stimulation pulses to at least one cardiac chamber of a heart of a patient,
   wherein at least one of the stimulation pulses has a first stimulation setting configured to reduce end diastolic volume (EDV) in the heart of the patient and at least one of the stimulation pulses has a second stimulation setting different from the first stimulation setting;
   reducing, by delivery of the stimulation pattern over the time period of at least three months, the end diastolic volume (EDV) by at least 5%,
   maintaining, by delivery of the stimulation pattern over the time period of at least three months, the end diastolic volume (EDV) in the heart of the patient on average at such reduced volume for the time period of at least three months, and
   maintaining, by delivery of the stimulation pattern over the time period of at least three months, blood pressure of the patient within an average pressure of ±10% as compared to a pretreatment blood pressure value for the time period of at least three months.

6. The method of claim 5, wherein the time period is at least twenty-four months, and wherein the maintaining the end diastolic volume (EDV) comprises maintaining the end diastolic volume (EDV) on average at such reduced volume for the time period of at least twenty-four months.

7. The method of claim 5, wherein the stimulation pattern is configured to reduce cardiac strain, as measured by wall tension, by at least 2% and maintain the cardiac strain on average at such reduced strain for the time period.

8. The method of claim 5, wherein the stimulation pattern is configured to limit reduction in ejection fraction of the heart to a maximum of 6% reduction and a time average of 2% reduction.

9. The method of claim 5, wherein the stimulation pattern is configured to prevent cardiac remodeling in the patient.

10. The method of claim 5, further comprising:
applying the stimulation pattern at a stimulation pattern configuration for a first period;
sensing cardiac strain for the first period; and
adjusting the stimulation pattern configuration according to the sensing.

11. The method of claim 5, wherein the first stimulation setting is configured to reduce the end diastolic volume (EDV) by at least 5% and the second stimulation setting is configured to reduce a baroreflex response or adaptation to the reduction in the end diastolic volume (EDV).

12. The method of claim 5, wherein the stimulation pattern is configured to reduce a baroreflex response or adaptation to the reduction in the end diastolic volume (EDV).

13. The method of claim 5, wherein the first stimulation setting is configured to reduce the end diastolic volume (EDV) by at least 5% and the second stimulation setting is configured to reduce a neuronal response or adaptation to the reduction in the end diastolic volume (EDV).

14. The method of claim 5, wherein the stimulation pattern is configured to reduce a neuronal response or adaptation to the reduction in the end diastolic volume (EDV).

15. The method of claim 5, wherein the first stimulation setting is configured to reduce the end diastolic volume (EDV) by at least 5% and the second stimulation setting is configured to increase hormonal secretion.

16. The method of claim 5, wherein the stimulation pattern is configured to increase hormonal secretion.

17. The method of claim 5, wherein the first stimulation setting comprises stimulating a ventricle of the heart 40-90 milliseconds after atrial activation.

18. The method of claim 17, wherein the second stimulation setting comprises stimulating an atrium of the heart to thereby produce atrial stimulation.

19. The method of claim 5, wherein the second stimulation setting comprises stimulating a ventricle of the heart 100-180 milliseconds after atrial activation.

20. The method of claim 5, wherein the second stimulation setting comprises allowing a natural AV delay to occur.

21. The method of claim 5, wherein the stimulation pattern includes at least 4 consecutive heartbeats having the first stimulation setting for every 1 consecutive heartbeat having the second stimulation setting.

22. The method of claim 21, wherein the stimulation pattern includes at least 8 consecutive heartbeats having the first stimulation setting for every 1 consecutive heartbeat having the second stimulation setting.

23. The method of claim 5, wherein the stimulation pattern comprises at least one stimulation pulse having a third stimulation setting different from the first and second stimulation settings.

24. The method of claim 5, wherein the cardiac malfunction is associated with an increase in at least one of end systolic volume (ESV) or end diastolic volume (EDV).

25. The method of claim 5, wherein the cardiac malfunction is congestive heart failure.

26. The method of claim 5, further comprising:
applying the stimulation pattern at a stimulation pattern configuration for a first period;
sensing at least one parameter indicative of at least one of end systolic volume (ESV), end diastolic volume (EDV), cardiac strain, or blood pressure for the first period; and
adjusting the stimulation pattern configuration according to the sensing.

27. The method of claim 26, wherein the adjusting the stimulation pattern includes adjusting at least one of the first stimulation setting or the second stimulation setting.

28. The method of claim 26, wherein the adjusting the stimulation pattern configuration includes adjusting at least one of the number or proportion of at least one of stimulation pulses having the first stimulation setting or stimulation pulses having the second stimulation setting within the stimulation pattern.

29. The method of claim 5, wherein the stimulation pattern limits, during the time period, reduction in ejection fraction of the heart to a maximum of 6% reduction.

30. A method for treating cardiac malfunction, comprising:
delivering over a time period of at least twenty-four months a stimulation pattern of stimulation pulses to at least one cardiac chamber of a heart of a patient,
wherein at least one of the stimulation pulses has a first stimulation setting that stimulates a ventricle of the heart 40-90 milliseconds after atrial activation and reduces end diastolic volume (EDV) in the heart of the patient,
wherein at least one of the stimulation pulses has a second stimulation setting that stimulates the ventricle 100-180 milliseconds after atrial activation, and
wherein the stimulation pattern includes at least 4 consecutive heartbeats having the first stimulation setting for every 1 consecutive heartbeat having the second stimulation setting,
such that the stimulation pattern:
reduces, during the time period, the end diastolic volume (EDV) by an average of at least 5%,
maintains, during the time period, the end diastolic volume (EDV) in the heart of the patient on average at such reduced volume, and
maintains, during the time period, blood pressure of the patient within an average pressure of ±10% as compared to a pretreatment blood pressure value.

* * * * *